United States Patent

Guttmann Cherniak

[19]

[11] Patent Number: 4,603,698

[45] Date of Patent: Aug. 5, 1986

[54] SYSTEM OF PODIATRIC APPLIANCES INDEPENDENTLY ADJUSTABLY SECURABLE ON INNER SOLE-LIKE BASE PLATE

[76] Inventor: Jaime Guttmann Cherniak, Ave. Tiradentes No. 10, Centro Commercial Dalyn, Ens. Naco, Santo Domingo, Dominican Republic

[21] Appl. No.: 608,562

[22] Filed: May 9, 1984

[51] Int. Cl.⁴ ............................................. A61F 5/14
[52] U.S. Cl. .................................. 128/603; 128/581; 128/615; 128/621; 128/81 R; 36/31; 36/43
[58] Field of Search .............. 128/68, 81 R, 602, 603, 128/581, 582, 583, 586, 596; 36/31, 43, 44

[56] References Cited

U.S. PATENT DOCUMENTS

| | | | |
|---|---|---|---|
| 1,585,938 | 5/1926 | Pease | 128/603 X |
| 1,867,679 | 7/1932 | Riehle et al. | 128/81 R |
| 2,478,664 | 8/1949 | Morrow et al. | 36/31 |
| 2,510,654 | 6/1950 | Pepin | 128/81 R X |
| 2,818,062 | 12/1957 | Braxton | 128/81 R |
| 4,476,638 | 10/1984 | Quacquarini et al. | 36/31 X |

FOREIGN PATENT DOCUMENTS

| | | | |
|---|---|---|---|
| 563654 | 6/1957 | Italy | 128/68 |
| 192991 | 2/1923 | United Kingdom | 128/603 |
| 277856 | 9/1927 | United Kingdom | 128/603 |

*Primary Examiner*—Richard J. Apley
*Assistant Examiner*—David J. Brown
*Attorney, Agent, or Firm*—Cushman, Darby & Cushman

[57] ABSTRACT

An inner sole-like base plate is provided of stiffly flexible material provided with a grid of a multiplicity of mounting sites, e.g. small holes. A plurality of different podiatric appliances are provided, each in a range of graduated sizes or intensities and/or in an adjustable manner. Each of the appliances is provided with securement devices, such as two or more wire tabs, which extend from the appliance and are adapted for connection to the base plate at such of the mounting sites as are prescribed or otherwise determined to best suit the resulting construction to the individual wearer. In some instances the resulting construction is meant to be worn as an insert for conventional footwear or orthopedic footwear, and in other instances sandal-fashion either by itself or inside or outside a wearer's socks, possibly then enclosed in a shoe or other covering. Some of the appliances are adapted to be worn on the foot without a base plate.

18 Claims, 38 Drawing Figures

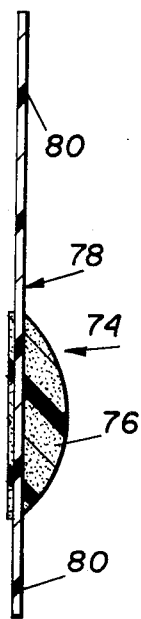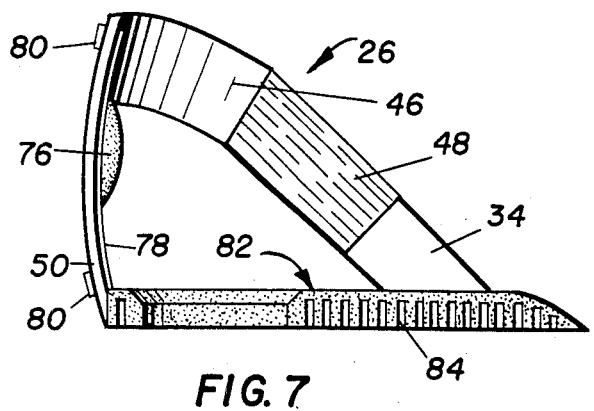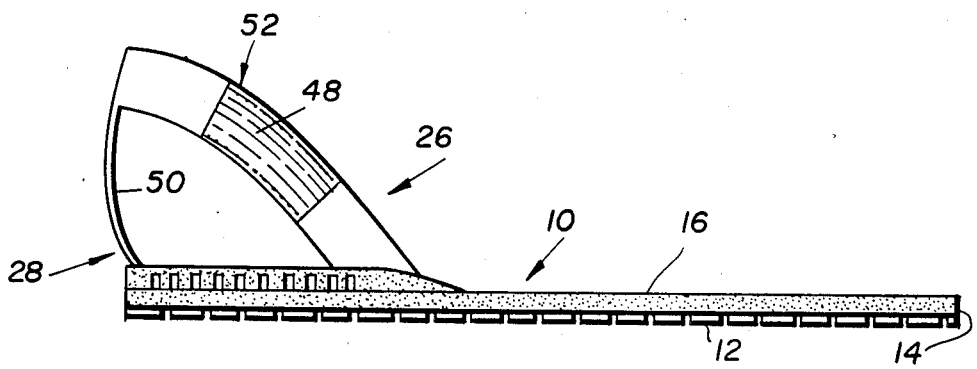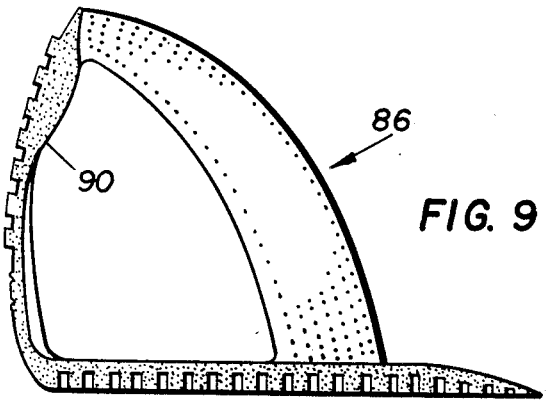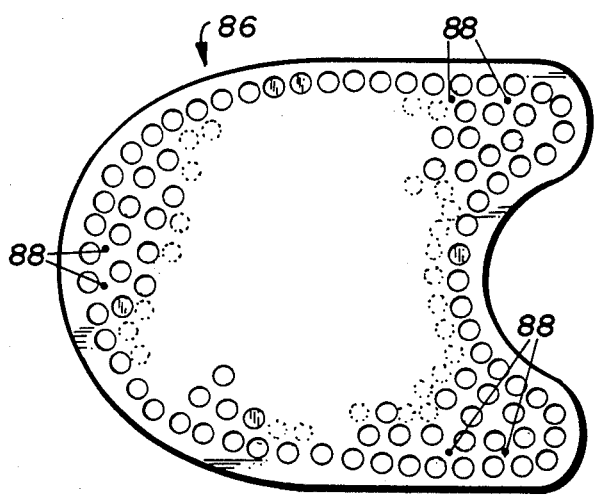

FIG. 12
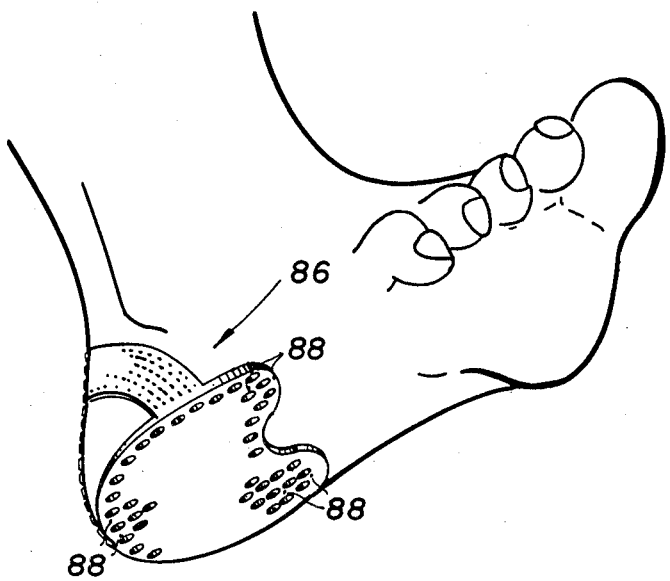
FIG. 13
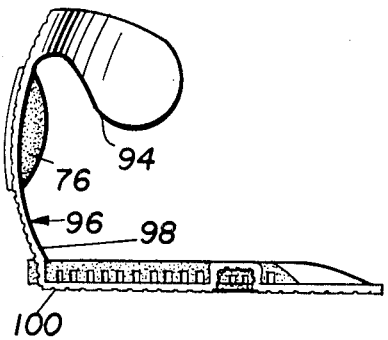
FIG. 15
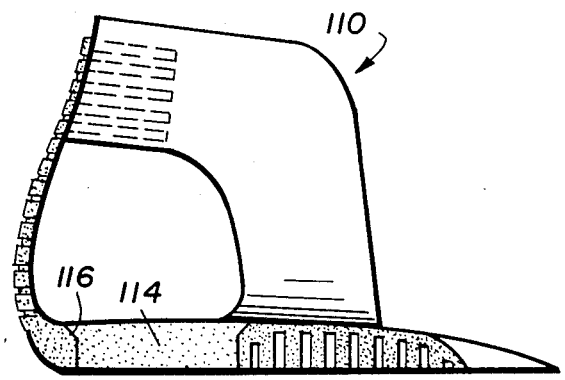
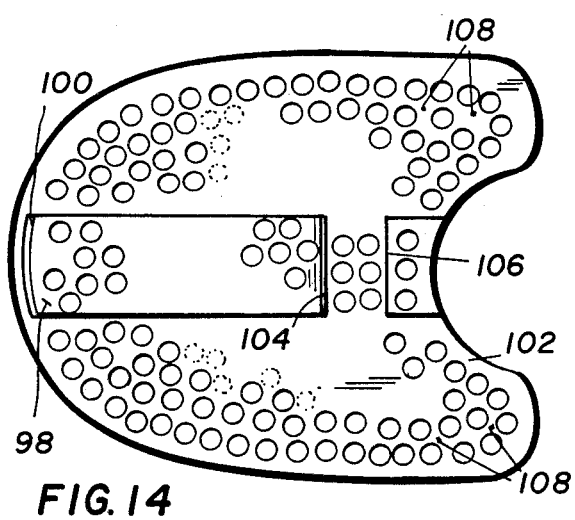
FIG. 14
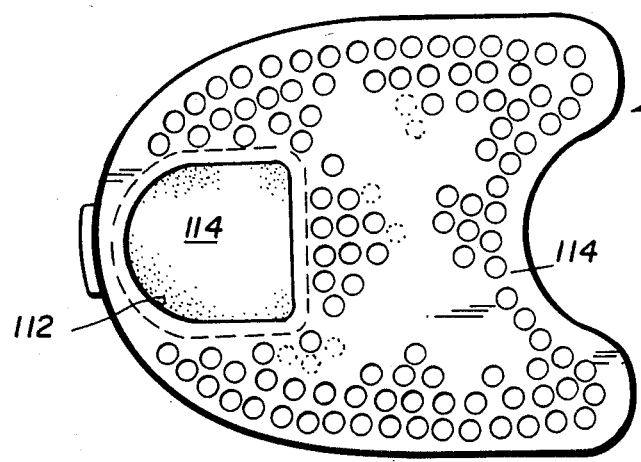
FIG. 16

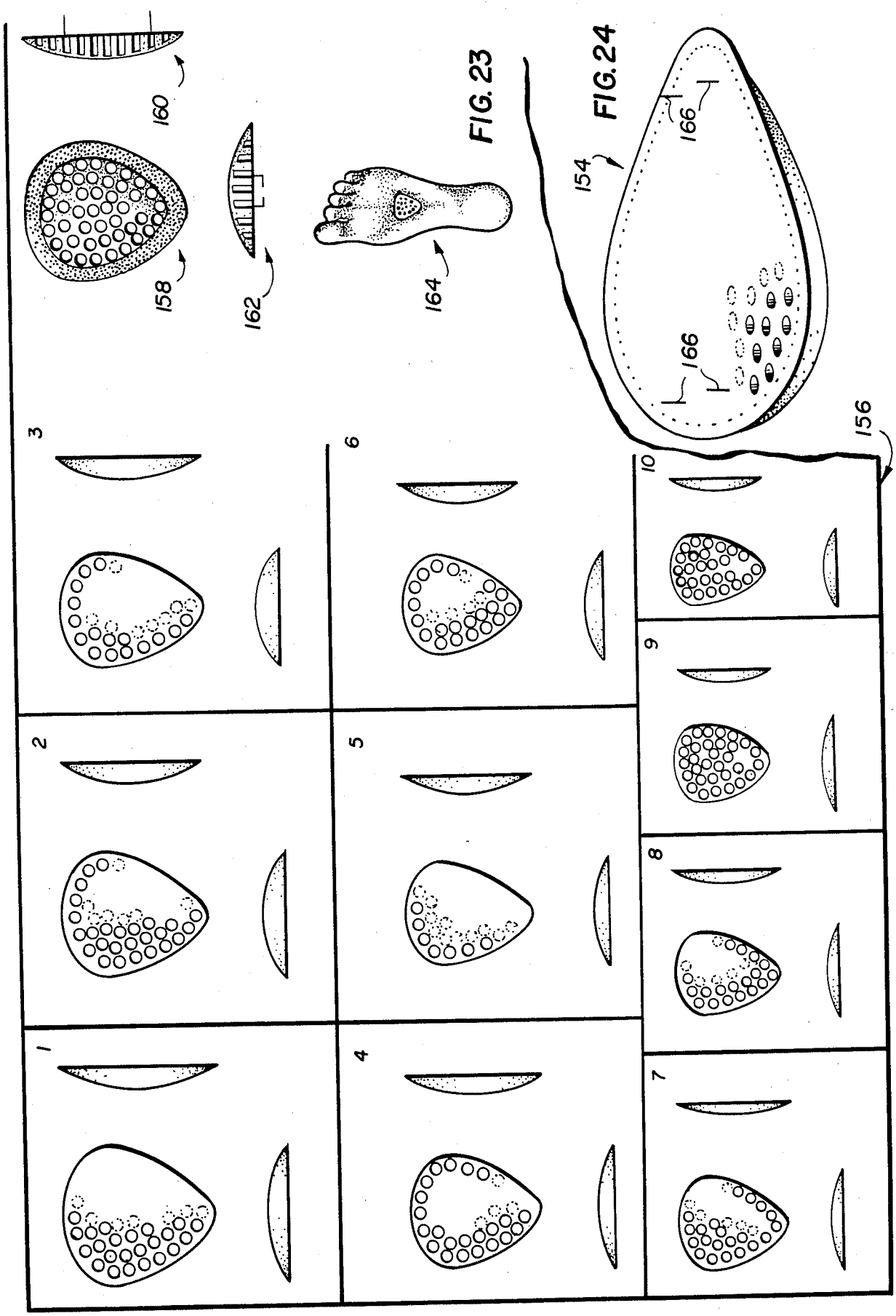

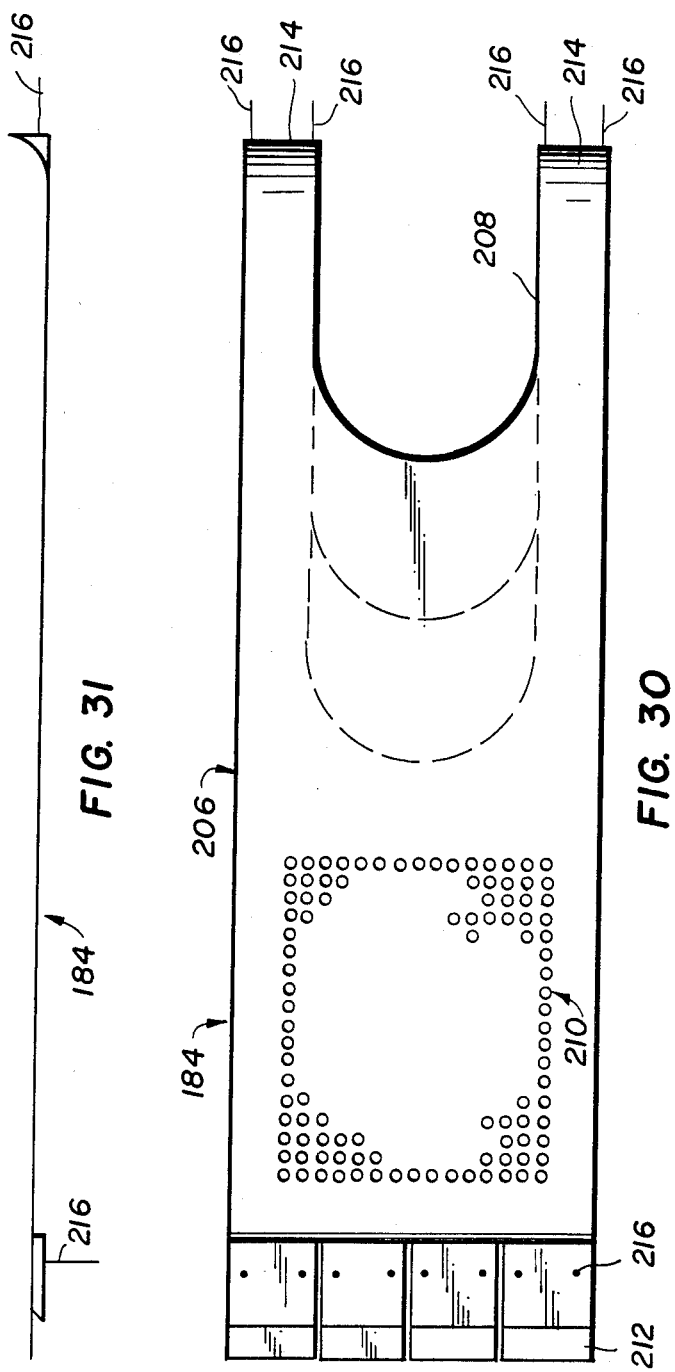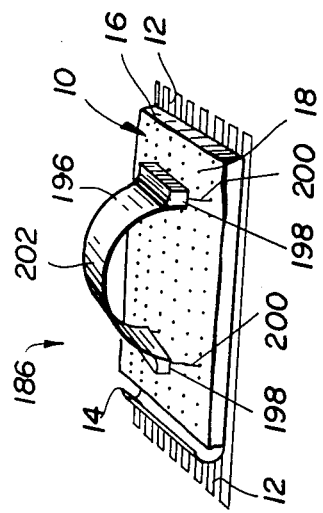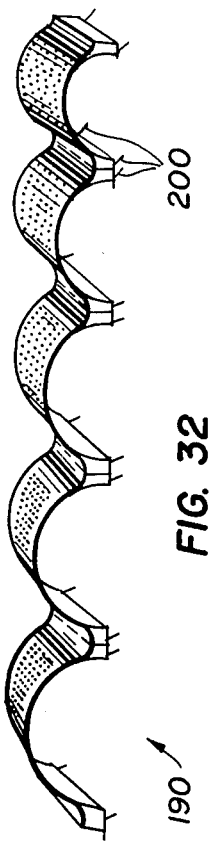
FIG. 31
FIG. 30
FIG. 33
FIG. 32

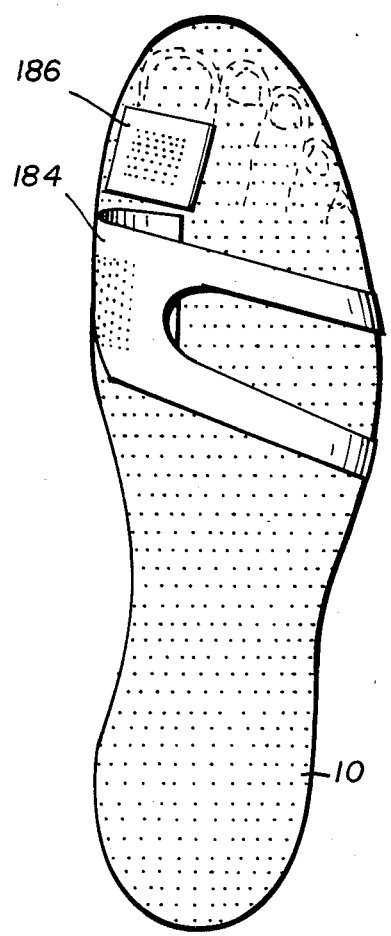
FIG. 34
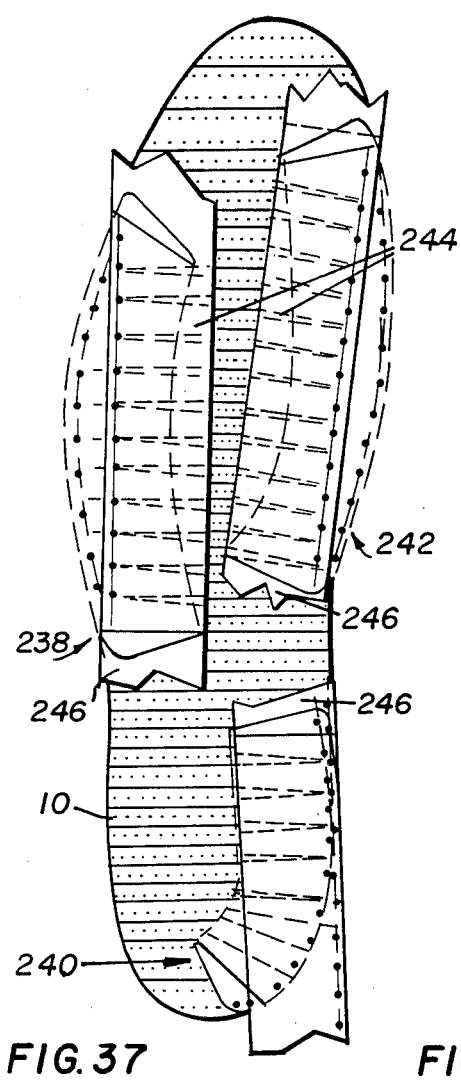
FIG. 37
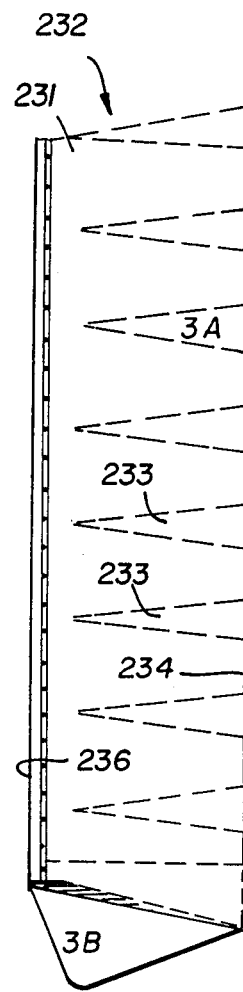
FIG. 38
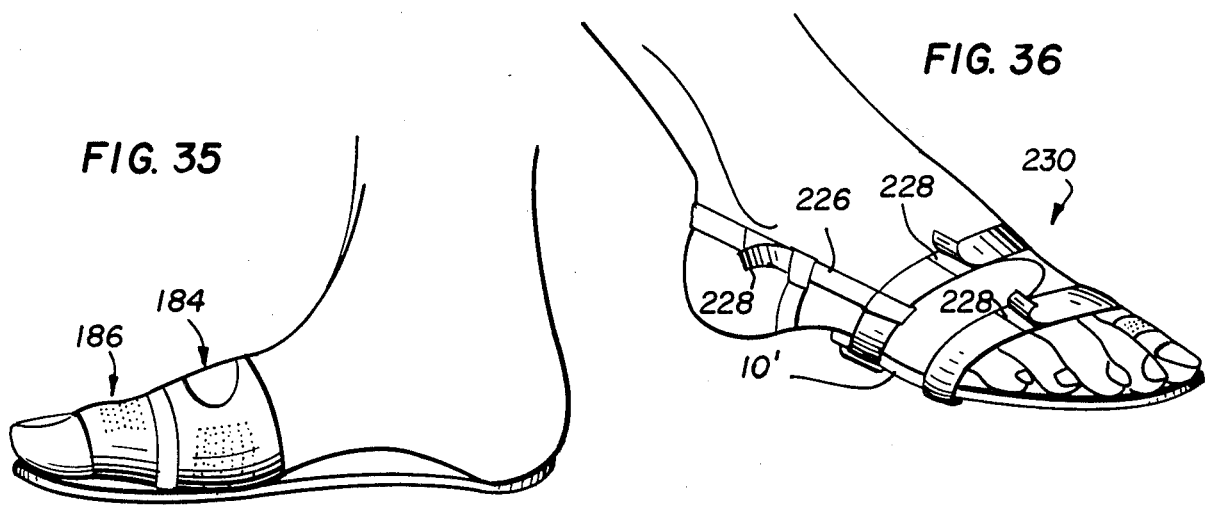
FIG. 35
FIG. 36

SYSTEM OF PODIATRIC APPLIANCES INDEPENDENTLY ADJUSTABLY SECURABLE ON INNER SOLE-LIKE BASE PLATE

BACKGROUND OF THE INVENTION

For many people who suffer from injuries, disease or congenital malformation, conventional footwear, such as shoes, cannot be worn at all, or cannot be worn, as is, without great discomfort, the risk of exacerbating the condition, or without aiding in recovery or alleviation of pain. There are others, who have normal feet or ones with only slight abnormalities who desire to or must adapt their feet to a wrong size or otherwise ill-fitting shoe. This sometimes happens when a person's sense of fashion triumphs over their common sense upon seeing a particularly attractive shoe at the store. Other times it happens when a person has bought a pair of shoes on a day when their feet were at an extreme from their average size, and now that the fit is found to be poor, the user cannot afford to or will not discontinue the wearing of those shoes. Yet other times it happens when a perfectly good pair of shoes stretches out or changes shape because the wearer got caught in a sudden rainstorm, or has feet which perspire enough to wet the shoes.

Accordingly, there has been engendered an industry of manufacturing special orthopedic footwear, custom shoes and various podiatric appliances, some of which are intended to be designed for and fitted to the afflicted person or to their footwear by podiatrists, orthopedists and related professionals, and others of which are mass produced and sold over-the-counter at shoe stores, pharmacies and the like.

From the present inventor's perspective the present state of the art is highly imperfect in that it provides at one extreme expensive, custom-made special footwear and appliances which few of the afflicted can afford or obtain even under public health or insurance company health benefit programs, and in that it provides at the other extreme often largely ineffective, often counter-productive, often self-prescribed, largely "one-size-fits-all", often flimsy pads, patches, and nostrums, many of which will not withstand being cleaned or being temporarily removed while the wearer bathes. Thus in the present state of the art, there appears to be a gap in the center, between what is too expensive to reach its natural market and what is too cheap to be effective.

SUMMARY OF THE INVENTION

An inner sole-like base plate is provided of stiffly flexible material provided with a grid of a multiplicity of mounting sites, e.g. small holes. A plurality of different podiatric appliances are provided, each in a range of graduated sizes or intensities and/or in an adjustable manner. Each of the appliances is provided with securement devices, such as two or more wire tabs, which extend from the appliance and are adapted for connection to the base plate at such of the mounting sites as are prescribed or otherwise determined to best suit the resulting construction to the individual wearer. In some instances the resulting construction is meant to be worn as an insert for conventional footwear or orthopedic footwear, and in other instances sandal-fashion either by itself or inside or outside a wearer's socks, possibly then enclosed in a shoe or other covering. Some of the appliances are adapted to be worn on the foot without a base plate.

The principles of the invention will be further discussed with reference to the drawings wherein preferred embodiments are shown. The specifics illustrated in the drawings are intended to exemplify, rather than limit, aspects of the invention as defined in the claims.

BRIEF DESCRIPTION OF THE DRAWINGS

In the Drawings

FIG. 6 is a fragmentary longitudinal sectional view of a modified mounting for the heel adapter;

FIG. 7 is a side elevational view of a heel appliance assembled from the heel band blank of FIG. 4, a heel cushion and the adjustably mounted heel adapter of FIG. 6; and FIG. 8 is a side elevational view of the heel appliance of FIG. 7 (minus the adjustably-mounted heel adapter), mounted to the stiffly-flexible insole-like base plate of FIGS. 1-3.

FIG. 9 is a side elevational view, partly in section, of a one-piece heel band appliance;

FIG. 10 is a top plan view thereof;

FIG. 11 is a bottom plan view thereof; and

FIG. 12 is a perspective view of a specimen of the one-piece heel band appliance being worn, the securements by which this appliance may be adjustably mounted to the stiffly-flexible insole-like base plate of FIGS. 1-3;

FIG. 13 is a side elevation view, partly in section, of another embodiment of the heel band appliance; and FIG. 14 is a bottom plan view thereof.

FIG. 15 is a side elevation view, partly in section, of another embodiment of the heel appliance, this one being shown having its heel pad centrally provided with a well receiving a tablet of especially soft resilient material for accommodating a calcaneal spur of the wearer; and FIG. 16 is a bottom plan view thereof.

FIG. 23 is a schematic view illustrating as a selection chart, a range of sizes for a metatarsal tear body;

FIG. 24 is a perspective view from below of a specimen of the metatarsal tear body (a top plan view thereof being shown in FIG. 18).

FIG. 30 is a plan view of the blank for a bunion support appliance;

FIG. 31 is a side elevation view thereof;

FIG. 32 is a perspective view of a strip of graduated size hammer toe support appliances ready to be cut apart and a selected one installed on the base plate;

FIG. 33 is a fragmentary exploded perspective view showing a selected hammer toe support appliance being installed on the base plate;

FIG. 34 is a top plan view of a base plate of FIGS. 1-3 provided with both a selected hammer toe support appliance of FIG. 33 and a selected bunion support appliance of FIGS. 30 and 31; and FIG. 35 is a schematic illustration of a wearer's foot and lower leg, with the wearer's foot being shown provided with the assembly shown in FIG. 34.

FIG. 36 is a perspective view of the assembly of FIG. 35, modified to be worn sandal fashion.

FIG. 37 is a top plan view of a base plate provided with leveling bars in accordance with principles of the present invention; and FIG. 38 is a fragmentary top plan view of stock for providing the leveling bars.

DETAILED DESCRIPTION

The system of podiatric appliances of the present invention in its presently preferred embodiments includes an inner sole-like base plate 10.

Figure 1:
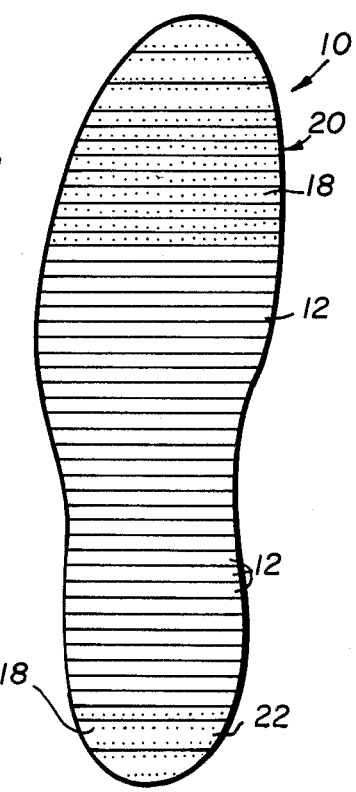
FIG. 1 is a top plan view of a stiffly-flexible insole-like base plate provided with a grid of securement sites in accordance with principles of the present invention.
Figure 2:
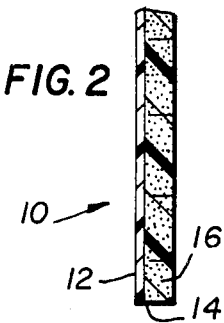
FIG. 2 is an expanded-scale fragmentary longitudinal sectional view thereof on line 2—2 of FIG. 1.

As shown in FIGS. 1 and 2, this base plate 10 may be a comparatively thin element that is made of stiffly flexible material, preferably being more flexible about longitudinally spaced, transversely extending axes than about transversally spaced, longitudinally extending axes. To that end, the base plate may be fabricated by adhering or otherwise laminating a plurality of parallel, closely spaced narrow strips 12 of metal or synthetic plastic sheet, e.g. made of stainless steel or polyvinyl acetate and similar in thickness and stiffness to a collar stay or credit card, to a flexible backing or cover sheet 14, e.g. made of fabric, felt, artificial leather or other synthetic plastic sheeting, e.g. of the type conventionally used in the manufacture of inner soles for shoes. A layer 16 of resilient foamed plastic or rubber material such as is conventionally used in the manufacture of cushioned insoles or uppers of shoes may be adhered or otherwise laminated to or juxtaposed face-to-face with the upper or lower face of the base plate 10. In some instances, the base plate may be provided as an integrally formed object, e.g. made of synthetic skinned foamed plastic material with or without embedded stiffeners such as the strips 12. The opposite face of the strips 12 from that to which the cover layer is applied may also have a layer of fabric or the like adhered or otherwise laminated thereto, for sandwiching the strips 12 inside the base plate 10. The base plate 10 typically has a thickness in the same range as conventional insoles and cushion insole inserts.

In most instances, the base plate 10 would be stamped-out, cut-out or otherwise severed from a wide sheet of indeterminate length, having the strips 12 extending transversally of the sheet. Each of the strips 12 is, for instance, about six millimeters wide and a fraction of a millimeter thick and the strips 12 are spaced a fraction of a millimeter apart. In the process of manufacturing the sheet from which the base plates 10 are to be severed, a network, array or grid of attachment or securement sites is provided, preferably by boring or drilling a pattern of tiny holes 18 through the composite sheet, with each site being located within the borders of a strip 12. Although it is within the contemplation of the invention to provide such sites on only a portion of the base plate 10, as is suggested in the heel and toe regions of FIG. 1, by preference, the pattern of sites 18 extends uniformly over the whole of the face of the base plate, e.g. as is suggested in FIGS. 18 and 19. For instance, the holes 18 may be provided in rows 20, one row per strip 12, with each row coinciding with the center line of a respective strip 12. As is suggested at 22 in FIGS. 1 and 19, where less flexibility is desired in a certain region, the stiffening strips may be widened, and in such an instance may be provided with correspondingly more rows of sites 18, in order to preserve the uniformity of the pattern of sites 18.

Figure 3:
FIG. 3 is a schematic plan view illustrating as on a selection chart, a range of sizes for the base plate.

It is contemplated that the base plates 10 would be provided in a range of sizes, and in "lefts" and "rights". A suggestion of a range of sizes is provided in the chart shown in FIG. 3, in which the indicia 24 may indicate sizes in order to facilitate ordering, supplying, prescribing, purchasing and the like. In general, each nominal size of base plate 10 would be shaped and sized to fit within a correspondingly sized shoe, much as an insert or replacement insole is received.

By means of applied indicia or contrasting coloration or matching with a graph paper template in the nature of a prescription, the individual sites 18 may all be assigned unique "addresses", e.g. so that a selected appliance can be mounted to a selected base plate 10 at a prescribed or determined location.

One typical appliance constructed and arranged for mounting on the base plate 10 is shown in and described with reference to FIGS. 4–8. This appliance 26 is meant to be associated with the wearer's heel and is herein sometimes called a heel band. A typical use for such a heel band is to adapt a shoe down in size to fit a smaller foot than that shoe would otherwise fit.

Figure 4:
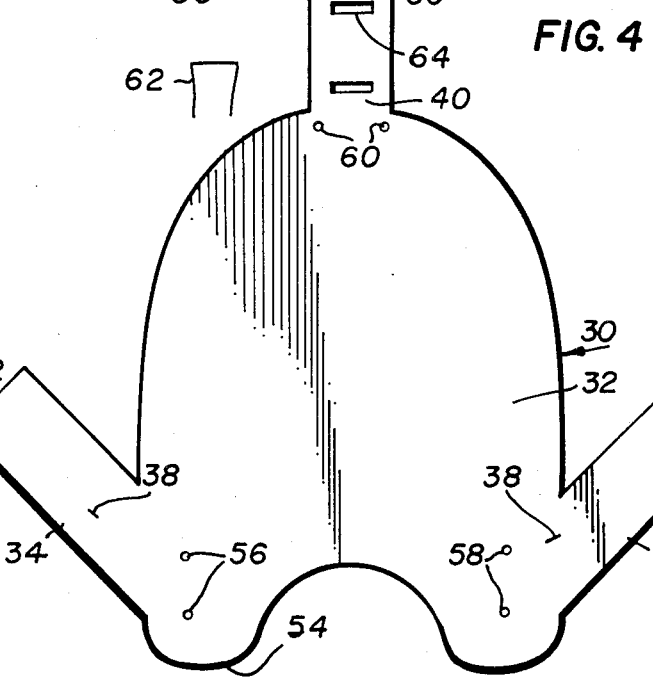
FIG. 4 is a top plan view of a blank for fabricating a first embodiment of heel band.

As is suggested in FIG. 4, the body 28 of the heel band 26 may be made from a body blank 30 e.g. cut or otherwise severed from a sheet of stock material, e.g. synthetic plastic resin sheet, artificial leather, rubber or the like. The blank 30 is shown having a main, under heel pad or region 32, provided with two tabs 34 which extend at an acute angle at the sides, and a T-shaped tab 36 at the rear, in order to fabricate the blank 30 into a body 28, the tabs 34 and 36 are folded up at 38 and 40, respectively. Then the ends 42 of the respective tabs 34 are secured to the ends 44 of the respective arms 46 of the T-shaped tab 36, e.g. through the intermediacy of respective short strips 48 of elastic belting, such as is conventionally used for garment waist-banding. Thus there is provided a rear strut 50 that is generally vertically oriented but slightly concave forwards, and two elasticized struts 52 which angle or curve forwards and downwards until they meet the under heel region 32 at 38, at the lateral margins of the under heel region 32, near its anterior edge 54.

It should now be noticed that a set of attachment sites 56, 58, 60 is shown provided on the blank 30, e.g. within the under heel region 32; near the base of each strut 50, 52. These sites 56–60 may include holes e.g. arranged in patterns as shown, or marker dots indicating where a staple or similar fastener is to be applied.

For securing the body 28 on the base plate 10, fine wires 62 may be inserted through the pairs of sites 56, 58, 60 and through the respective prescribed or determined holes 18 on the base plate and folded under, staple fashion, or twisted together garbage bag tie fashion or a secure registration otherwise provided and fixed between respective sites 56, 58, 60 on the body 28 and the proper sites 18 of the base plate 10.

As with the base plate 10 as is described above with reference to FIG. 3, the blank 30 and resulting body 28 preferably are provided in a range of progressively different sizes.

There are times when the body 28 as mounted to the base plate 10 as so far described will occupy enough space in the heel area of the user's shoe to make a loose shoe fit comfortably or acceptably.

Figure 5:
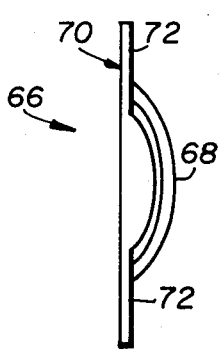
FIG. 5 is a side elevation view of a heel adapter for selective and adjustable mounting to the vertical posterior strut of the heel band.

It should now be noticed that the vertical rear strut 50 is shown provided with a series of horizontally, transversally extending slots 64 spaced vertically from one another in a column. These slots 64 provide mounting sites for adjustably, removably mounting a selected or prescribed adapter body 66. The adapter body 66 as shown in FIG. 5 includes a centrally disposed enlargement 68 made of resilient rubber, synthetic plastic fabric and fleece or the like, on the rear of which a vertically elongated stay 70 of stiffly flexible material is secured so as to have tabs 72 extending above and below the thickened portion 68. The adapter body 66 is mounted on the front of the rear strut 50 by inserting the tabs 72 through a selected two of the slots 64 so as to dispose the enlargement at the proper level. The adapter body 66 may be molded as a unitary body, e.g. with a strap of flexible metal embedded in it to provide the tabs 72. By preference the adapter body 66 is provided in a range of thicknesses, shapes or relative positions of enlargements 68, so that a proper one may be prescribed or determined.

A modified adapter body 74 is shown by itself in FIG. 6. Here, the enlargement 76 is frictionally mounted or adhered on the stay 78 at a desired level so that when the tabs 80 of the stay 78 are mounted in the respective two slots provided on the rear strut 50 of the heel band as shown in FIG. 7, the enlargement 76 will be carried at the desired height.

An elaboration is shown in FIG. 7, where a cushion 82 is superimposed on the upper surface of the under heel region 32 of the body 28 so as to cover the same. This cushion 82 preferably is molded of resilient rubber or the like and provided with perforations, corrugations, wells or the like 84 so as to contribute to the cushioning, step-muffling effect provided thereby. The cushion 82 may be simply deposited in place, or attached or adhered in any convenient manner upon the under heel region 32 of the body 28.

The assembled structure shown in FIG. 7, preferably is mounted on a base plate 10 as described hereinabove and inserted in a shoe either before or in association with insertion of the wearer's foot into a shoe. In the latter instance the base plate-mounted FIG. 7 structure is first mounted to the person's heel much as one would put on the heel portion of a sandal. The person may put on a sock or the like before donning the base plate-mounted FIG. 7 structure, or after donning the base plate-mounted FIG. 7 structure, or omit wearing a sock. In any event, the elastic strips 48 tend to pull the structure against the person's heel so as to mount the structure to the person. In some instances the wearer may prefer to put on the FIG. 7 structure by itself, i.e. without it being secured to a base plate 10. In such an instance, all of the above-described wearing alternatives remain available, e.g. whether to put the device on the foot or in the shoe, whether to wear a sock, and, if so, whether to wear the FIG. 7 structure inside or outside the sock.

FIGS. 9–12 show a modification of the FIG. 7 structure wherein all of the separately made and assembled parts of the FIG. 7 structure are molded, e.g. of flexible, resilient synthetic plastic material, e.g. of an elastomer, rubber or the like as an integral, one-piece cushioned, thickened adapter-providing heel band structure 86. The FIG. 9 structure 86 is shown self-mounted on a person's heel in FIG. 12. In both FIG. 12 and FIG. 11, the mounting sites 88 which may be used for optionally mounting the structure 86 on a base plate 10 as described above are illustrated. The sites 88 may be holes, spots, or places where end portions of embedded twister wires, or of end portions of embedded staple-like elements or the like emerge to be inserted through respective holes 18 in the base plate 10 and twisted together, bent over, adhered or the like.

Once again, as with all of the elements disclosed herein, the structure 86 of FIGS. 9–12 preferably is provided in a range of sizes and, e.g. with a range of thicknesses of adapter portion 90.

In another version 92 of the heel band, shown in FIGS. 13 and 14, the side struts 94 are truncated into ears for resiliently clamping against the sides of the person's foot near the person's heel. The T-shaped tab member 96 has an elongated central leg portion 98 which bends from vertical to horizontal at 100 and extends under the resilient heel pad 102 and forwardly, passing up through the transversally extending vertically opening slot at 104, then down through the similar slot at 106 and further forwards so as to be interlocked and secured with the heel pad 102. Before the leg 98 is bent and inserted, an enlargement adapter body, e.g. of the type shown in FIG. 6 may be positioned and secured thereon at the prescribed or determined height. Similarly, the bend 100 is provided at such a place along the length of the leg 98 as to place the ears 94 at the proper level to grasp the person's foot. Sites 108 for mounting the heel band 92 to a base plate in the manner described above are shown in FIG. 14.

FIGS. 15 and 16 illustrate on another one-piece heel band 110 similar to the one shown in FIG. 9, a feature that can be provided on this or any of the versions of the heel band, particularly, that a cavity, well, central opening or the like 112 is molded into or cut from the resilient heel pad 114 so as to permit a calcaneal spur or other similarly positioned abnormality, growth, tender place or the like to be positioned over the opening 112. In such an instance, the person's weight on that foot is principally carried by the surrounding area and not on the abnormal or tender place. By preference an insert 114 of especially soft, spongy material is mounted in the opening 112. This insert 114 preferably is made to be removable, so that it may be replaced when worn, or when an insert of another thickness, degree of resiliency or the like is needed. As is indicated at 116, the sidewall of the opening 112 preferably flares near the top and the spongy plug 114 is similarly tapered, so as to avoid presenting a sharp discontinuity of support to the person's foot at the perimeter of the spongy plug 114.

Figure 17:
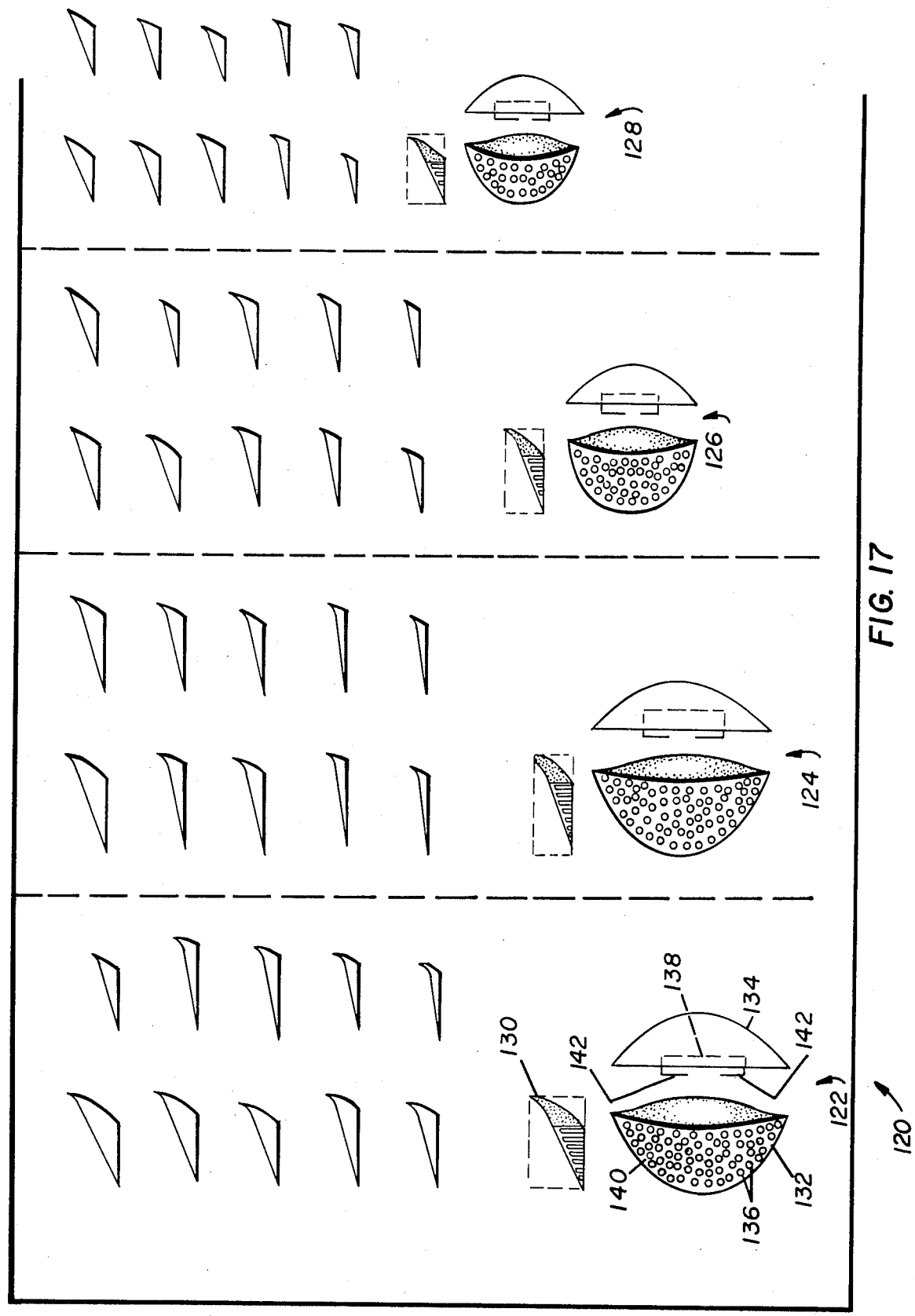
FIG. 17 is a schematic plan view illustrating as a selection chart, a range of sizes for an arch support body.
Figure 18:
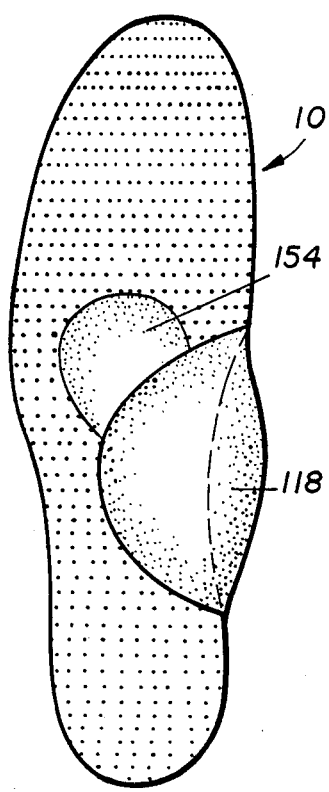
FIG. 18 is a top plan view of a stiffly flexible insole-like base plate of FIGS. 1-3, provided with an arch support body of FIG. 17 (and with a metatarsal tear body of FIGS. 23 and 24)
Figure 19:
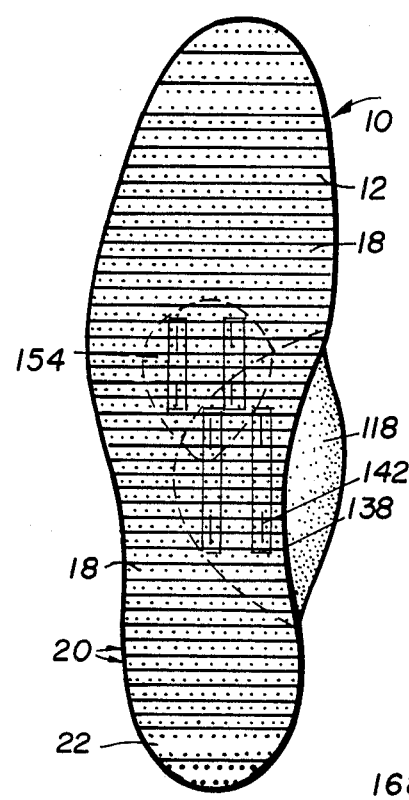
FIG. 19 is a bottom plan view of the assembly shown in FIG. 18.

Another type of podiatric appliance, an arch support body 118, which can be similarly mounted to the base plate 10 is shown by itself in a range of sizes in the chart 120 in FIG. 17, and is mounted to the base plate 10 in FIGS. 18 and 19.

In the chart, a typical range of sizes for the arch support body 118, sometimes familiarly termed a "cookie" are depicted in four series 122, 124, 126, 128. At the bottom of each series, a typical example of the arch support body 118 is shown at 130 in transverse vertical section, at 132 in bottom plan and at 134 in lateral elevation. Each body 118 preferably is molded of resilient rubber or plastic complete with pores, cells, wells or the like 136 in the manner of arch support bodies which are conventionally used in running shoes or the like.

However, by preference, as with the appliances hereinbefore described, a plurality of securement means sites 138 are preferably provided on each body 118 so as to be accessible at the underside 140 thereof. In the instances depicted, the securement means sites 138 are where the ends 142 of embedded U-shaped wires emerge from the underside 140. Accordingly, the selected arch support body may be mounted at a prescribed or otherwise selected site on a base plate 10 by inserting the wire ends 142 down through respective holes 18 and bending them over, twisting them together or otherwise securing them.

Figure 21:
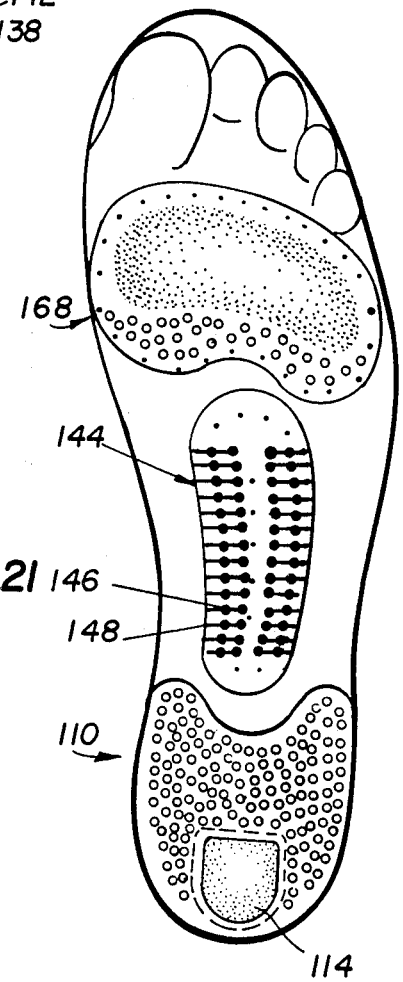
FIG. 21 is a bottom plan view of one of the bridge support bodies.
Figure 22:
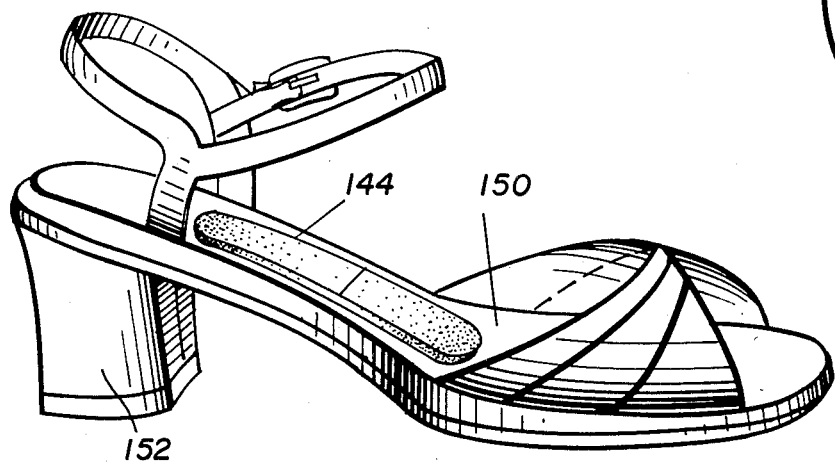
FIG. 22 is a perspective view showing the bridge support body of FIG. 21 secured in a shoe on the insole.
Figure 20:
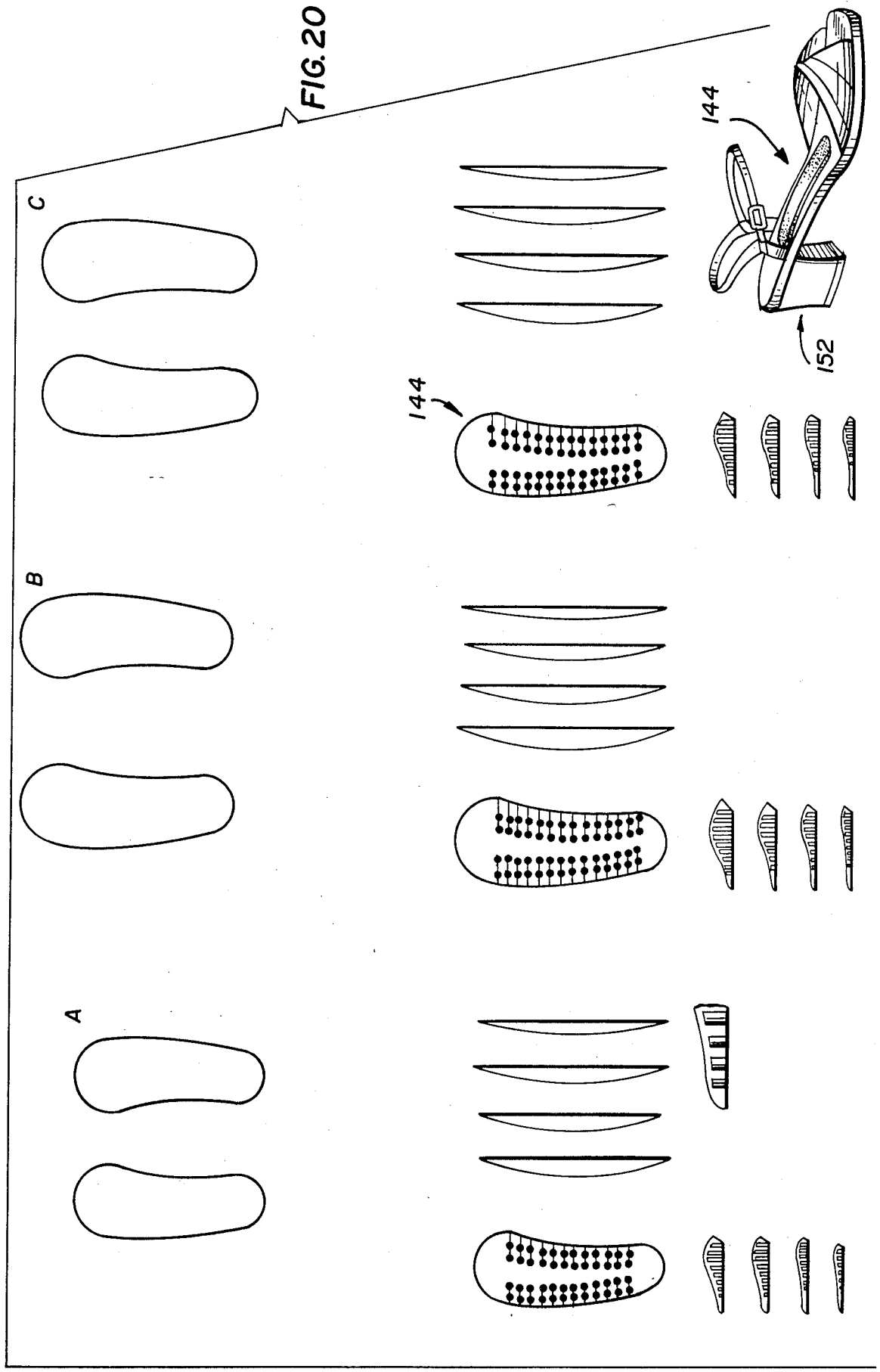
FIG. 20 is a schematic plan view illustrating as a selection chart, a range of sizes for a bridge support body.
Figure 25:
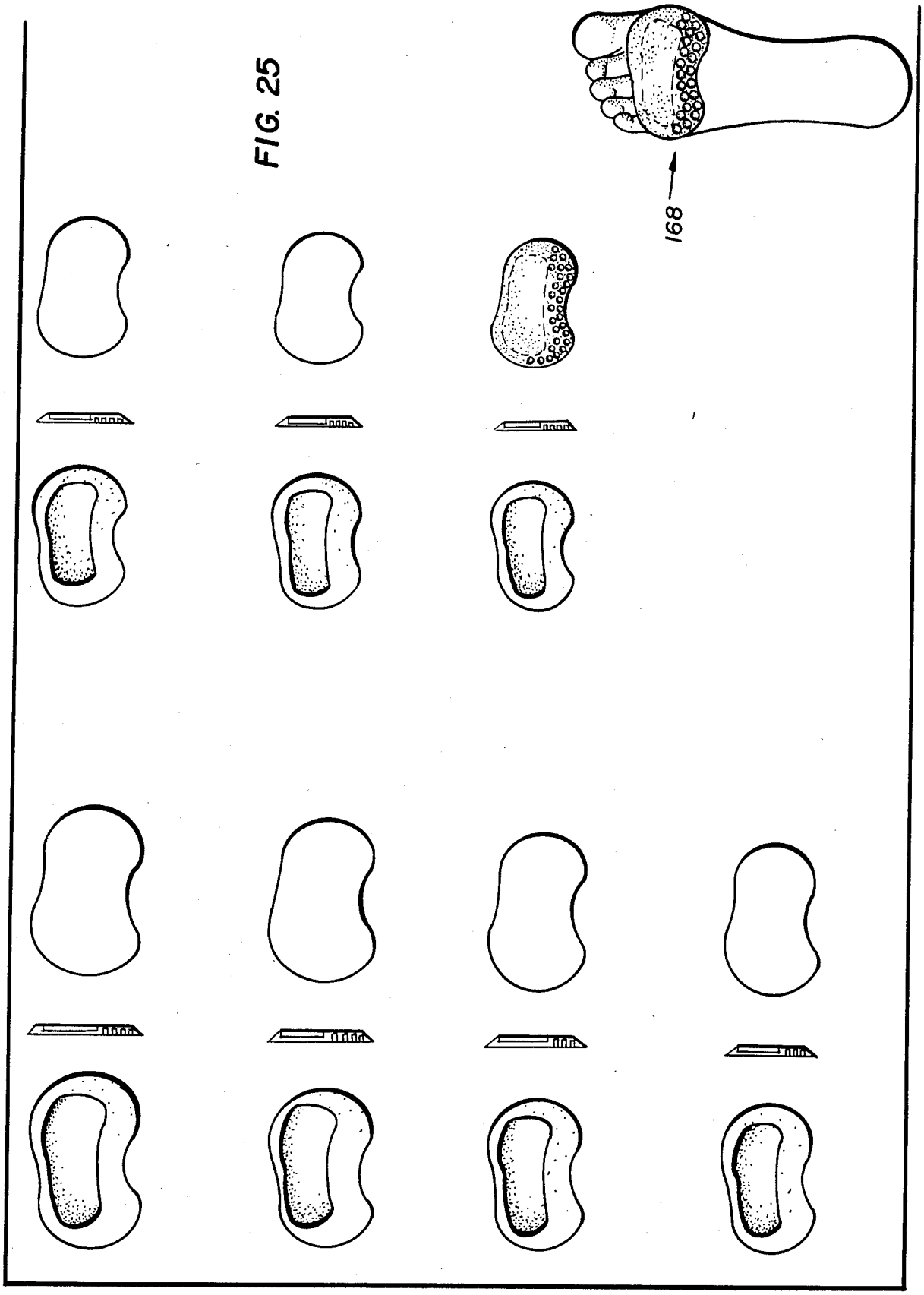
FIG. 25 is a schematic view illustrating as a selection chart, a range of sizes for a metatarsal cushioning body.
Figure 26:
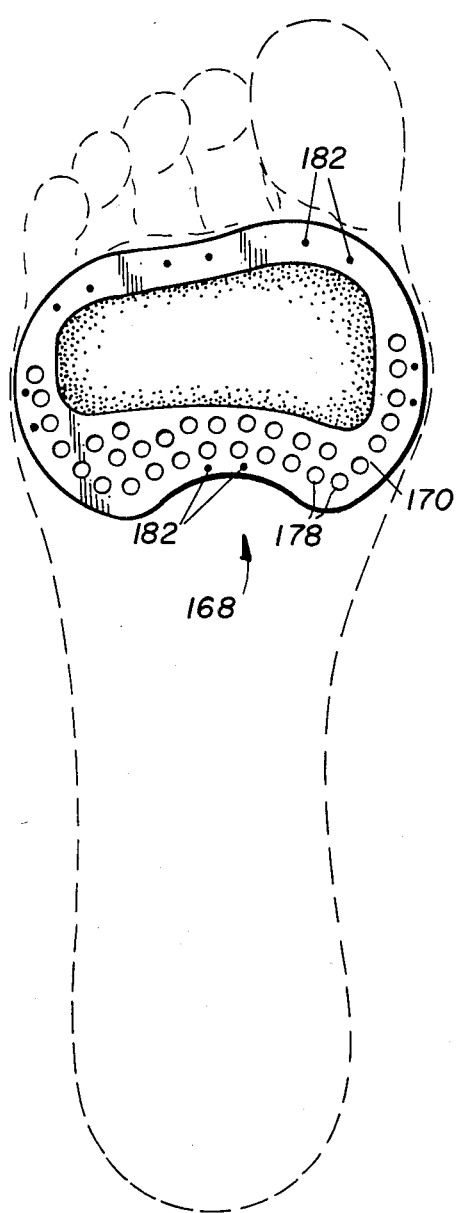
FIG. 26 is a bottom plan view of a specimen of the metatarsal cushioning body superimposed on the outline of a foot.
Figure 27:
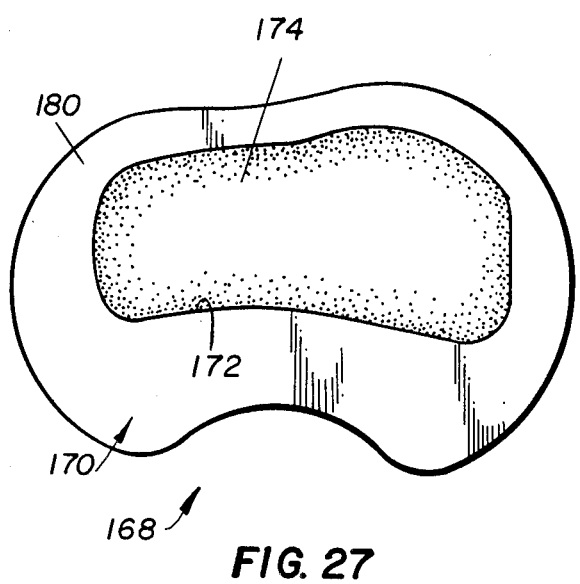
FIG. 27 is a top plan view thereof.
Figure 28:
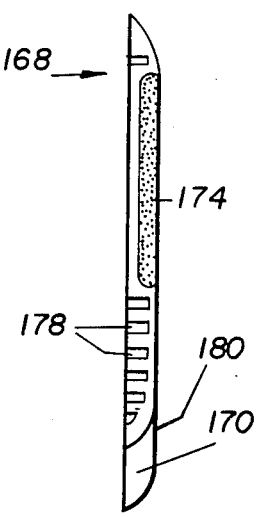
FIG. 28 is a cross-sectional view thereof.

A further appliance 144 is illustrated in FIGS. 20-22. It may be made in much the same way, and of the same materials as the arch support body 118, but because it is intended to be mounted at a different place so as to be located as a bridge support more centrally of the foot than an arch support, it has a different profile, e.g. as depicted. The appliance 144 typically would be used to fill in empty space left in a shoe between the wearer's foot sole and the usual insole of the wearer's shoe, so that the person's body weight is more evenly distributed on their foot. As is the arch support, the bridge support 144 preferably is molded of flexible, resilient, rubbery material and is ported as at 146 to add to its cushioning effect and facilitate air circulation. At least some of the cavities 146 preferably are open to the sides as is illustrated at 148.

As an alternative to be secured to a base plate 10 that is separate from the shoe, by means such as are disclosed hereinabove, the bridge support 144, and/or others of the appliances may be similarly secured to a base plate 150 in the form of an insole that is conventionally united to a shoe 152 as the insole of that shoe.

A further appliance 154 is illustrated in FIGS. 23, 24, 18 and 19. It may be made in much the same way, and of the same materials as the bridge support 144, but because it is intended to be mounted at a somewhat different place so as to function as a metatarsal tear, it has a different profile, e.g. as depicted. The appliance 154 serves to muffle the wearer's footsteps, help to relieve and rest the metatarsal bones and more evenly distribute the weight of the person. FIG. 23 shows a chart 156 typically depicting a range of ten profile sizes and for each profile size a range of three thicknesses for a metatarsal tear appliance. At the right of the chart, a representative one of the metatarsal tear applicances is shown in bottom plan view at 158, in longitudinal section at 160, in transverse section at 162 and in bottom plan as properly juxtaposed on the underside of a wearer's foot at 164. The chart is principally for aid in prescribing or ordering a selected size of appliance 154, but also serves to illustrate the desired size range availability. The preferred fastener wire ends which may be used in the manner described above in relation to other appliances for securing the selected metatarsal tear on a base plate 10 are illustrated at 166.

A further appliance 168 is illustrated in FIGS. 25-28. It may be made in much the same way, and of much the same materials as the bridge support 144 (and as the spongy plug of the appliance shown in FIGS. 15 and 16), but because it is intended to be mounted at a somewhat different place so as to function as a metatarsal cushion, it has a different profile, e.g. as depicted. The appliance 168 includes a body portion 170 having a generally bean-shaped oval profile with an upwardly open central well or opening 172 which is filled with a plug 174 of especially soft, resilient spongy material such as sponge rubber. The outer body portion 170 is molded of resilient rubber, plastic or the like and provided with downwardly open ports 178 for providing pneumatic cushioning. The upper surface 180 of this appliance as with the others if so shown, preferably is smooth. Fasteners 182 much as above described in relation to others of the appliances, are shown for securing the selected metatarsal cushion appliance to a base plate 10.

A bunion support appliance 184 and a hammer toe support appliance 186 are shown and described together in relation to FIGS. 29-36, inasmuch as usually but not essentially, the two would be prescribed to be used together for accommodating or treating the same foot condition.

"Bunion" is the name commonly given to a foot condition in which the first metatarsal bone is malformed and the great toe is twisted. Heretofore there has not been available, to the present inventor's knowledge, an orthopedic device for permitting patients with such a condition to walk normally while wearing shoes. The present invention provides such a device, as well as one which can be worn, without shoes, as a sandal-like item of footwear.

Figure 29:
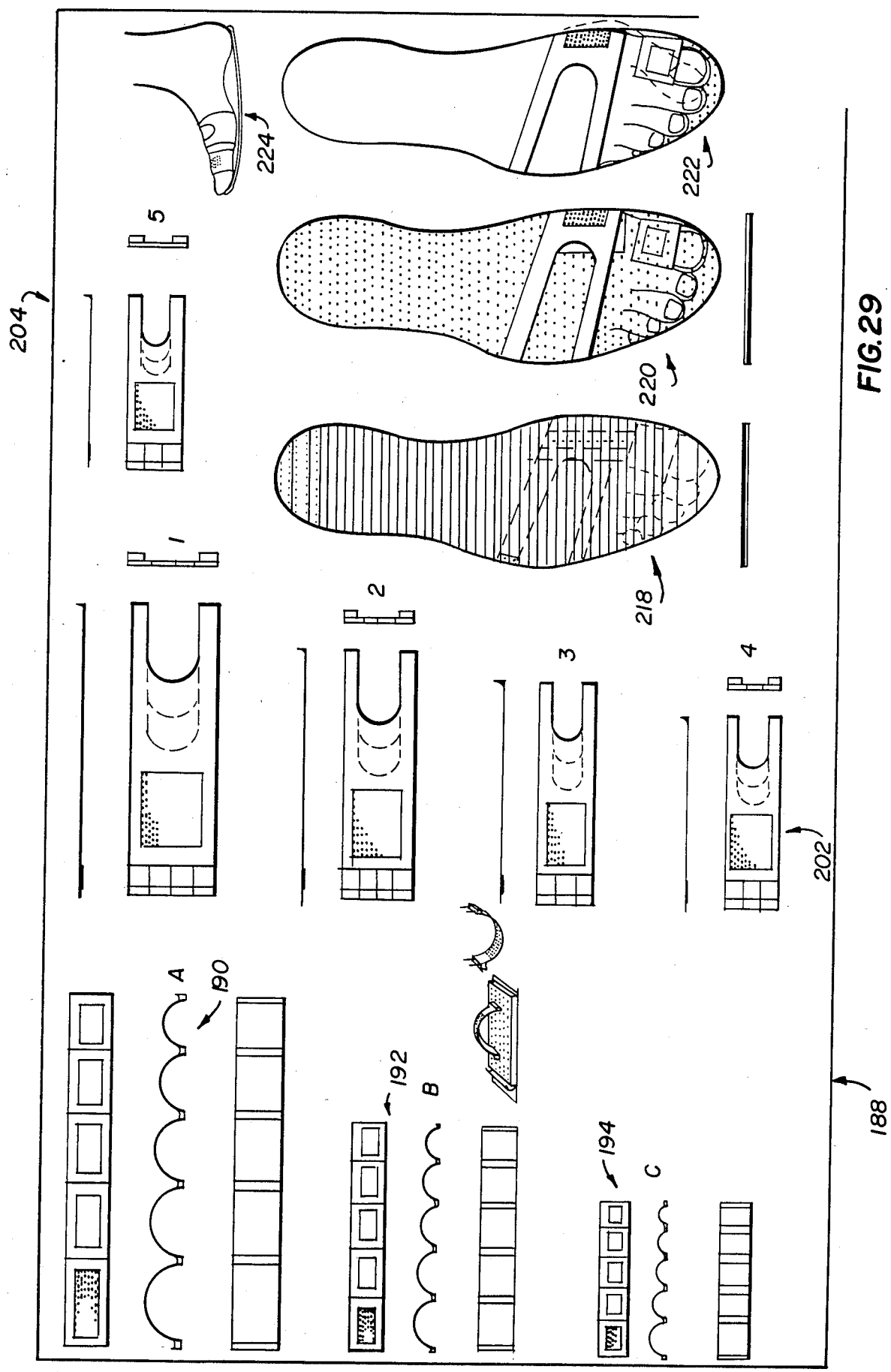
FIG. 29 is a schematic view illustrating as a selection chart, a range of sizes for bunion and hammer toe support appliances adjustably mounted on a base plate in accordance with the present invention.

In FIG. 29 there is shown a chart 188 showing at the left a typical range of sizes of stock material 190, 192, 194 for the hammer toe support. The stock material 190, 192, 194 is shown comprising a plurality of individual hammer toe support appliances in a plurality of series of graduated sizes, e.g. five to a strip. In practice, once the proper size had been determined, the strip containing that appliance would be ordered and the selected hammer toe support appliance 186 cut therefrom, e.g. using a sharp knife. Each hammer toe support appliance 186 is shown comprising an arched band 196 having left and right bases 198, each provided with a set of embedded wires having ends 200 which project down so that they may be inserted down through prescribed or selected holes 18 in a selected base plate 10 and bent, twisted or otherwise secured on the underside of the base plate for securing the hammer toe support appliance 186 on the base plate 10. This appliance preferably is molded of resilient, flexible plastic or rubber material, with staple-like metal wires 200. Ventilation holes are shown grouped at the top of the arched band at 202.

At the center of the chart 188 there is a column 202 depicting a range of sizes of the bunion support appliance 184, a series of four widths, with a series of three lengths in each width is shown in this typical depiction; a further series is shown at 204.

The bunion support appliance 184 typically is constituted by a generally rectangular molded band 206 of flexible, resilient plastic or rubber material, having a deep U-shaped cut-out 208 opening centrally at one end, a field of ventilation openings 210 provided beyond the cut-out 208, and securement bases 212, 214 provided at opposite ends. The cut-out 208 is shown dividing the base 214 into two segments. Each base is shown provided with a plurality of embedded, staple-like securement wires 216, the emergent ends of which are to be downwardly inserted through respective holes 18 on the selected base plate 10 and twisted, bent over or otherwise secured or adhered on the underside of the base plate 10 to mount the bunion support appliance 184 in place.

In the instance of the appliance 184, when the blank thereof is shown laid out flat, as in FIGS. 30 and 31, the wires 216 on the base 212 point upwards, while those on the base 214 point downwards. However, as the appliance is installed in a preferred manner on the base plate 10, after the wires of the base 214 have been downwardly inserted and secured in place near the lateral edge of the base plate, the band 206 is arched and partially looped as it crosses the base plate 10 so that the base 212 becomes inverted and its wires 216 now point down and may be inserted downwards through selected holes 18 and secured near but not at the medial edge of the base plate 10. The sets of wires 216 are spaced far enough apart that in each instance the securement at each side is to a plurality of different ones of the stiffener strips 12. This mounting places the ventilation openings 210 closer to the medial edge of the base plate 10 than is the securement base 212.

At the right of the chart shown in FIG. 29, a bottom plan view of the typical resulting device is shown at 218 with the front portion of a wearer's foot suggested in dashed lines in relation thereto, a similar top plan view is shown at 220, with the effect of the device on the wearer's foot being suggested by comparison of the dashed and solid line showings at 222. A small scale elevational view of the device, as worn, is shown in the chart at 224, a larger scale view being provided in FIG. 35. Likewise, FIG. 34 is a larger scale version of the matter depicted in the chart of FIG. 29 at 220.

The device as shown in FIG. 35 may be worn barefooted, as a sandal, as shown. More typically, the wearer would first put on the appliance as shown, then pull on a sock and finally put on their shoe.

An alternate form is depicted in FIG. 36, where the unused rear portion of the base plate has been cut away, and a set of sandal straps 226, e.g. with hook-and-fleece fasteners, such as Velcro fasteners 228 provided, secured to the truncated base plate 10', so as to provide a podiatric appliance sandal 230 which will maintain its proper orientation on the foot even when worn without a shoe.

Finally, a leveling bar appliance 231 is shown and described with reference to FIGS. 37 and 38. According to this feature, there is provided a strip 232 of stock material which is wedge-shaped as seen in transverse cross-sectional view, and which has a series of wedge shaped segments 233 removed from its thinner edge 234 so that, while it remains continuous along its thicker edge 236, it may be curved to a greater or lesser degree as needed. Thus, in an instance where, through malformation, a person's foot is not suited to wear a shoe of normal appearance, one or more lengths of the strip 232 may be cut from the stock, curved as needed, and applied and mounted to a base plate 10 in order to provide custom leveling shims for raising, turning, separating or otherwise modifying corresponding parts of the wearer's foot in relation to a shoe. The stock preferably is made of stiffly resilient rubber or plastic, such as the material that rubber heels for brogue shoes is made of. The stock may be supplied in a range of heights and widths, and in long lengths, or in lengths that are at least as long as the longest length likely to be needed, e.g. twelve inches long.

In FIG. 37, three appliances 238, 240, 242 have been cut from the strip stock, curved and applied to the base plate 10. The strip stock may be supplied without cut out segments 233 removed, so that the practitioner can cut out and remove segments of any angular extent, as needed. Other portions may be removed as suggested at 244 where their presence is not helpful. Fabric tape 246 or other smooth covering may be adhered or otherwise secured on the exposed upper face of the leveling bars for comfort's sake. The leveling bars may be secured to the base plate using embedded wires in the same manner that is described above in relation to the other appliances. In the instance of any of the appliances, other means than wires may be used to augment or partly or wholly in place of the embedded wires for securing the appliances on the base plate. For instance the same kinds of adhesive that are used for attaching insoles to shoes, or outer soles or heels to shoes may be used in instances where position adjustment following a period of trial is not needed. Even in such cases, the provision of sites marked on the base plate which can be reliably matched with sites marked on the appliances to ensure precision in locating or reporting location of appliances on base plates is provided in accordance with the principles of the invention.

It should now be apparent that the system of podiatric appliances independently adjustably securable on inner sole-like base plate as described hereinabove, possesses each of the attributes set forth in the specification under the heading "Summary of the Invention" hereinbefore. Because it can be modified to some extent without departing from the principles thereof as they have been outlined and explained in this specification, the present invention should be understood as encompassing all such modifications as are within the spirit and scope of the following claims.

What is claimed is:

1. A podiatric appliance system, comprising:
   a stiffly flexible base plate having an outline approximating that of at least a portion of the length and width of a foot sole, in the manner of a conventional footwear inner sole;
   said base plate being more flexible about a series of longitudinally spaced, transversely extending axes thereof, than about longitudinally extending axes thereof;
   said base plate including a plurality of strips of stiffly flexible material, each of such a thickness as to be flexible about its own longitudinal axis each not more than six millimeters wide arranged with close spacing of less than one millimeter from strip to strip, in a series in a single layer, with each strip extending transversely of the base plate; and means flexibly uniting all of said strips, said uniting means being a layer of flexible material to which each of said strips is secured;

means providing a tangible grid of mounting sites on said base plate, extending in a uniform, predetermined pattern on all of at least one face of said base plate;

said mounting sites comprise closely spaced respective small, round holes provided vertically through each of said strips;

each said strip having said holes provided in at least one row of uniformly spaced holes, each of which rows extends lengthwise of the respective strip, which equates to transversally of the base plate;

a podiatric appliance constructed and arranged to have an operative portion thereof positioned in engaging relation with a respective portion of a foot of a wearer;

a mounting base provided on said podiatric appliance;

means providing at least two sets of spatially separated tangible securement sites on said mounting base of said podiatric appliance, said securement sites being constructed and arranged to be selectably juxtaposable in registry with a respective number of said mounting sites on said base plate so that such juxtapositions may be matched to a prescription, recorded or reported; and respective securement means constructed and arranged for securing said mounting base to said base plate at each place where a said securement site is juxtaposed in registry with a said mounting site;

said securement means comprising a plurality of small U-shaped wires round in transverse cross-section and having respective central portions embedded in said mounting base of said podiatric appliance, each wire having two end portions protruding from said mounting base nearer to the perimeter than to the center of such mounting base, including one end portion at each respective securement site; and said mounting sites being constructed and arranged to have respective ones of said wire protruding end portions inserted downwardly therethrough and bent under said base plate for securing said podiatric appliance on said base plate.

2. The podiatric appliance system of claim 1, wherein:
said podiatric appliance is a heel band.

3. The podiatric appliance system of claim 2, wherein:
said heel band has secured thereto a rear strut extending generally vertically upwardly from said mounting base and a band portion which extends both leftwardly and forwardly and rightwardly and forwardly from said rear strut, distally of said band portion being constructed and arranged to engage between left and right portions thereof the wearer's foot rearwardly of the wearer's ankle.

4. The podiatric appliance system of claim 3, wherein:
said rear strut has associated therewith a thickened adapter body which is constructed and arranged to fill a gap between the rear of the wearer's foot and rear quarters of a shoe worn on the wearer's foot.

5. The podiatric appliance system of claim 4, wherein:
said thickened adapter body is height adjustably mounted to said rear strut.

6. The podiatric appliance system of claim 5, wherein:
said thickened adapter body is removably and exchangeably mounted to said rear strut.

7. The podiatric appliance system of claim 3, wherein:
a pad of resilient, pneumatic cushioning material is provided on said mounting base of said heel band.

8. The podiatric appliance system of claim 7, wherein;
said pad includes a ring-shaped outer portion of more stiffly resilient material surrounding a well; a body of spongy, softer material being contained in said well for cushioning a respective portion of the wearer's foot.

9. The podiatric appliance system of claim 1, wherein;
said podiatric appliance is a metatarsal tear including a pad of resilient cushioning material integrated with said mounting base.

10. The podiatric appliance system of claim 1, wherein:
said podiatric appliance is a metatarsal cushion including a pad of resilient, pneumatic cushioning material integrated with said mounting base, said pad including a ring-shaped outer portion of more stiffly resilient material surrounding a well; a body of spongy, softer material being contained in said well for cushioning a respective portion of the wearer's foot.

11. The podiatric appliance system of claim 1, wherein:
said podiatric appliance is a bridge including a longitudinally elongated, trasnversally comparatively narrow pad of resilient cushioning material integrated with said mounting base.

12. The podiatric appliance system of claim 1, wherein:
said podiatric appliance is a bunion support including a band of resilient material, constructed and arranged to loop across the wearer's foot back of the wearer's toes, said mounting base being provided in at least two separated portions at opposite ends of said band, each such portion being provided with at least one said set of securement sites.

13. The podiatric appliance system of claim 1, wherein:
said podiatric appliance is a hammer toe support including a band of resilient material, constructed and arranged to loop across the wearer's great toe, said mounting base being provided in at least two separated portions at opposite ends of said band, each such portion being provided with one said set of securement sites.

14. The podiatric appliance system of claim 1, further including:
a second podiatric appliance constructed and arranged to have an operative portion thereof positioned in engaging relation with a respective portion of a foot of a wearer;

a mounting base provided on said second podiatric appliance;

means providing at least two sets of spatially separated tangible securement sites on said mounting base of said second podiatric appliance, said securement sites being constructed and arranged to be selectively juxtaposable in registry with a respective number of said mounting sites on said base plate so that such juxtapositions may be matched to a prescription, recorded, or reported; and respective securement means constructed and arranged for securing said mounting base of said second podiatric appliance to said base plate at each place where a said securement site of said second podiatric appliance is juxtaposed in registry with a said mounting site.

15. The podiatric appliance system of claim 14, wherein:

the first-described podiatric appliance is a bunion support including a band of resilient material, constructed and arranged to loop across the wearer's foot back of the wearer's toes, said mounting base being provided in at least two separated portions at opposite ends of said band, each such portion being provided with at least one said set of securement sites; and said second podiatric appliance is a hammer toe support including a band of resilient material, constructed and arranged to loop across the wearer's great toe, said mounting base being provided in at least two separated portions at opposite ends of said band, each such portion being provided with one said set of securement sites.

16. The podiatric appliance system of claim 1, wherein:

said podiatric appliance is a leveling bar including an elongated pad of resilient cushioning material integrated with said mounting base, said leveling bar being of generally triangular or wedge-shaped transverse cross-sectional shape and being adapted to be flexed prior to being secured to said base plate to provide variable curvature of said podiatric appliance in a horizontal plane.

17. The podiatric appliance system of claim 1, wherein:

said base plate further includes thong-like strap means secured thereto and fastener means provided on said strap means, whereby said base plate is constructed and arranged to be secured sandal fashion on a wearer's foot.

18. The podiatric appliance system of claim 15, wherein:

said base plate further includes thong-like strap means secured thereto and fastener means provided on said strap means, whereby said base plate is constructed and arranged to be secured sandal fashion on a wearer's foot.

* * * * *